Figure 1:
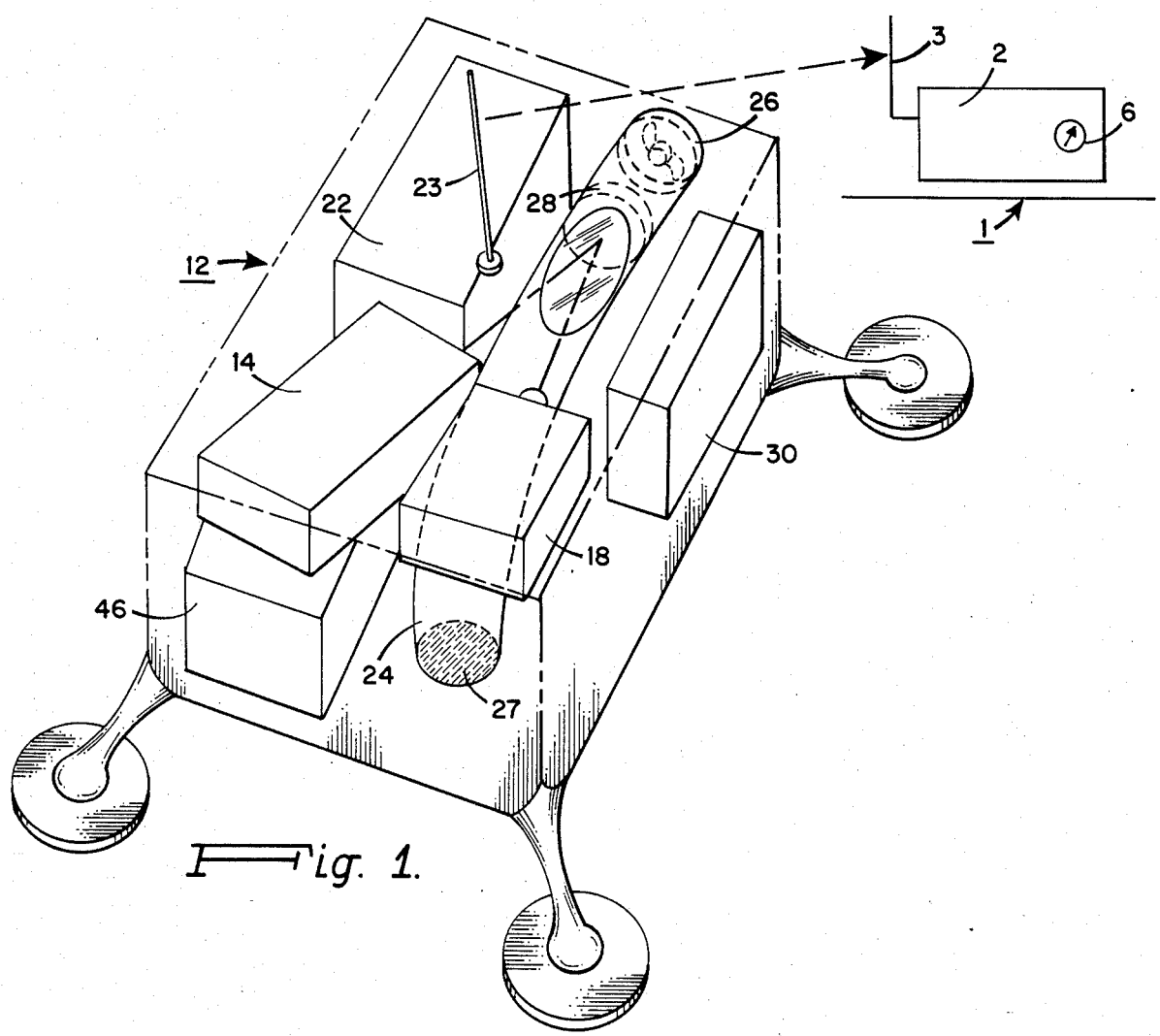

United States Patent [19]

Javan

[11] Patent Number: 4,651,010
[45] Date of Patent: Mar. 17, 1987

[54] METHOD AND APPARATUS FOR FLUORESCENT SENSING

[75] Inventor: Ali Javan, Cambridge, Mass.
[73] Assignee: Laser Science, Inc., Cambridge, Mass.
[21] Appl. No.: 617,165
[22] Filed: Jun. 4, 1984
[51] Int. Cl.$^4$ .................. G01N 21/64; G01N 21/75
[52] U.S. Cl. ........................ 250/458.1; 250/459.1; 250/461.1; 436/166; 436/172
[58] Field of Search ............... 250/458.1, 459.1, 461.1, 250/338 GA, 301, 304, 253; 436/166, 172, 104; 422/52

[56] References Cited

U.S. PATENT DOCUMENTS 3,603,952  9/1971  Smith ............................. 340/539
4,013,888  3/1977  Macias et al. ................... 250/304
4,394,573  7/1983  Correa et al. ................... 250/253

OTHER PUBLICATIONS

Edward J. Stone, "Ultraviolet Fluorescence Water Vapor Instrument for Aircraft", *Review of Scientific Instruments*, vol. 51, No. 5, (May 1980) pp. 677–678.

Primary Examiner—C. E. Fields
Assistant Examiner—Constantine Hannaher
Attorney, Agent, or Firm—E. Thorpe Barrett

[57] ABSTRACT

A sensing system for the detection of trace gases in the atmosphere or contaminates on a surface. Particular chemical substances are detected at remote points by placing a sensor unit in the vicinity of the area to be examined and illuminating the area with a laser beam generated by the sensor unit. An optical detector, also carried by the sensor unit, registers the fluorescence produced by the substance illuminated and relays this information by a telemetry link back to the base site. The utility of the system is broadened by providing a chemical reactant selected to react with the substance to be detected to produce a reaction product that fluoresces strongly at the wavelength of the laser light. The chemical reactant is carried by the sensor unit and is sprayed into the area to be examined. The sensor unit carrying the chemical reactant can also be used on location, for example, with a hand-held unit that sprays the chemical reactant on a surface suspected of being contaminated and detecting the resulting fluorescence of the reaction product.

5 Claims, 7 Drawing Figures

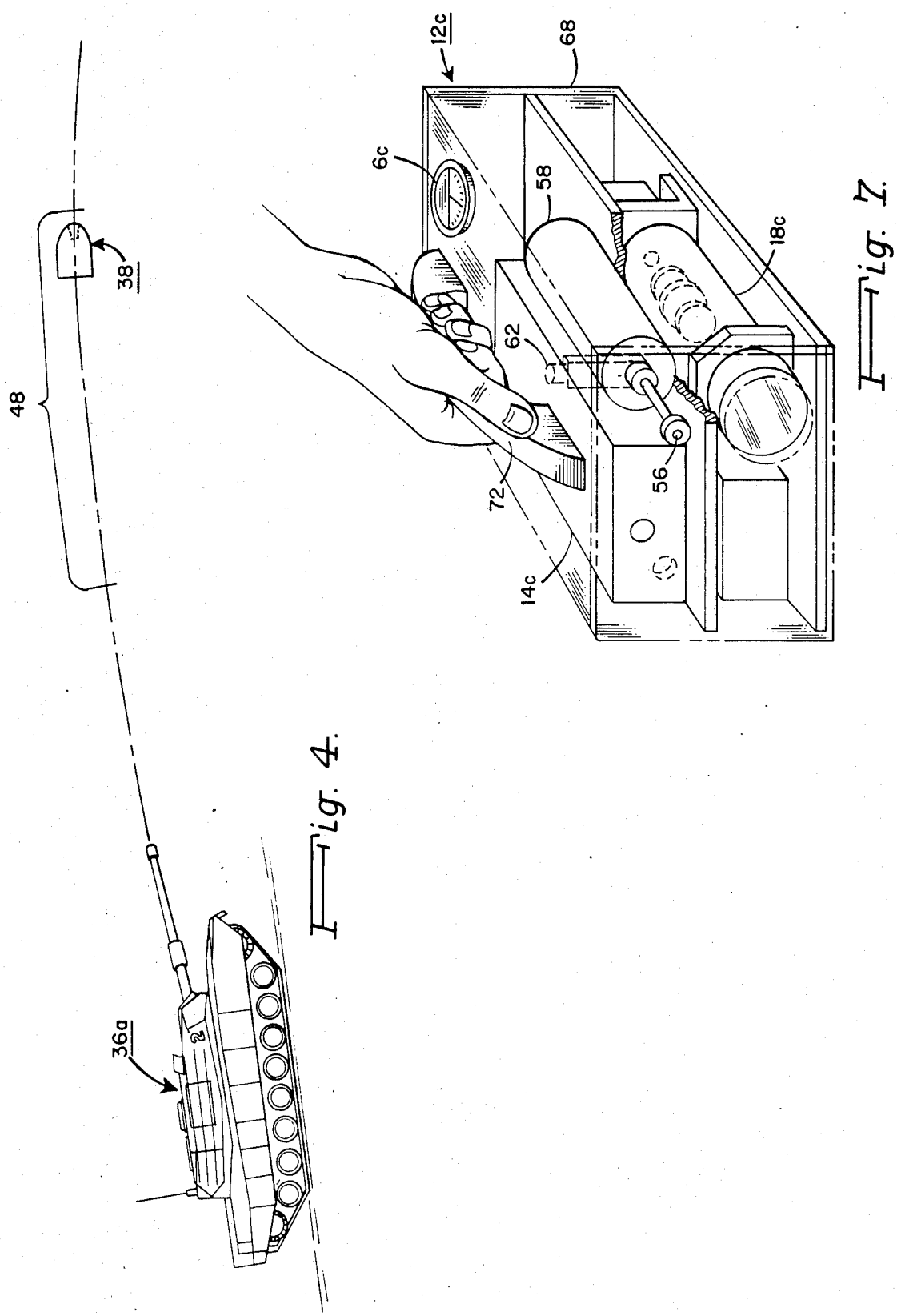

METHOD AND APPARATUS FOR FLUORESCENT SENSING

BACKGROUND OF THE INVENION

1. Field of the Invention

This invention relates to the sensing of surface contaminates and trace gases in the atmosphere and more particularly to the sensing of such materials at remote locations. In one embodiment, the detection results from fluorescence initiated by illumination with laser light, and in another arrangement, differential absorption of the substance serves as the basis for detection. Local or remote sensing may be accomplished by examination for fluorescence produced by a reaction product of a chemical reaction between the substance to be detected and a selected reagent.

2. Description of the Prior Art

Laser systems have been explored for the remote detection of chemical substances since early in the 1960's. One method has made use of fluoresence by the substance of interest initiated by laser light. In this method, the laser wavelength is selected to be near or at the peak of an absorption resonance in the trace gas or chemical element to be detected. This absorption resonance is selected to be one that causes strong fluorescence. In one such arrangement, a pulse of laser light is transmitted in the atmosphere in the area where the presence or absence of the particular substance is to be determined. A receiver, directed toward the radiant laser light, is arrranged to respond to the fluorescent radiation. For discriminating against spurious background fluorescence, a differential method is used. In this case, two successive pulses of different wavelengths are transmitted: one lying at a wavelength near or at the peak of the absorption line of the substance to be detected and the other at a wavelength appreciably removed from the absorption line. The fluorescent signals from the two pulses would appear predictably at different intensities making it possible to discriminate against spurious background fluorescence. In general, however, because the fluoresence from the substance at a remote location occurs over a solid angle of 4 pi radians, only a relatively weak signal is available to the receiver. This is equally true whether the fluorescence is from a reaction product or when the presence of biological agents is to be detected by the natural UV fluorescence. Such arrangements require a high energy laser beam and a sensitive receiver: the greater the distance between the substance to be detected and the location of the sensor unit, the greater must be the intensity of the laser light and the sensitivity of the receiver. The receiver usually requires narrow-band filters and a narrow field of view to discriminate against incident daylight. With the best of equipment, such arrangements are effective only over limited distances.

Contaminates in the air or on a surface have been detected by spraying a reactant chemical, selected to produce a reaction product having strong fluorescence, into the air or onto the surface and illuminating the area with laser light to cause fluorescence of the reaction product. Such arrangements have been limited to laboratory use and generally have been unsatisfactory for field use.

The detection of nerve gas and other chemical and biological agents is of great importance in military and other situations, but remote sensing of such agents has not been particularly sucessful. One problem, in addition to the problems of long-distance laser illumination and fluorescence detection, is caused by the fact that some substances do not have a strong fluorescence intensity that is readily detected. Another factor is that objectionable chemical agents may be camouflaged by releasing a chemical with similar fluorescence properties. In some instances, it is possible to provide a chemical reactant capable of reacting with the suspected contaminate to produce a reaction product selected to be one having a strong fluorescence.

A specific example is a remote sensor for agent specific detection of nerve gas soman (GB) with indole and sodium perborate in a mixture of acetone and water. From an early investigation in 1957 [See B. Gehauf and J. Goldenson, Anal. Chem., 29, 276 (1957)], it is known that in a two step process, the reaction produces indoxbyle, which fluoresces strongly when subjected to laser radiation in the 350 nm wavelength region. A XeF laser at 350 nm, or a nitrogen laser at 337 nm, can be used. The fluorescence spectrum peaks at 450 nm and has a width of about 50 nm. See Alan Hartford, Quarterly Progress Report AP-4-82:109, July 18, 1982, Page 1, Los Alamos National Laboratory, University of California, Los Alamos, N.M.

SUMMARY OF THE INVENTION

There are two major difficulties in the remote sensing of chemical substances by the detection of fluorescence. The first results when attempting to detect substances in which the fluorescence occurs over a broad and featureless unresolved line. This has been a major difficulty in the remote sensing of chemical and biological agents such as nerve gas where the presence of such agents can be camouflaged by introducing other chemical substances with similar fluorescence emission. One method of overcoming this difficulty, as pointed out above, is to spray into the area of the substance to be detected, a second chemical agent capable of selective reaction with the substance to be detected and whose reaction product is capable of strong fluorescence. The presence of the reaction product is determined by laser illumination of the reaction product at a strong absorption frequency. In accordance with this invention, such a chemical reactant is carried by the sensor unit that also includes a laser and an optical sensor and is arranged so that the reactant is sprayed into the area or onto the surface to be examined by laser illumination and optical scanning.

Another difficulty arises, as discussed above, because of the distance between the sensor unit and the area to be examined for the substance of interest. The difficulty of long distance laser illumination and equally long distance detection of fluorescence severly limits the capability for remote sensing.

The present invention overcomes these difficulties by placing the source of the laser illumination and the fluorescence detection at the site of the substance to be detected and transmitting the results to the measuring site by a telemetry signal.

To illuminate a substance from a distance with laser light of sufficient intensity to cause substantial fluorescence, requires a large and bulky laser system: one that is costly and not ideally suited for field operations. However, it is possible, by locating the laser adjacent the area to be examined for the presence of the substance, to make use of a low power laser; one that may be small, self-contained, have a short operating life, and be low in cost. Similarly, the detection problem can be solved by placing the fluorescence detector adjacent the area to be examined.

One example of an operating system may thus comprise a telemetry receiver at the base site and a remote sensor unit located in the vicinity of the area to be examined for the presence of a particular substance. The sensor unit includes a laser that radiates a relatively low-power beam, an optical detector that responds to the presence of the fluorescence, and a telemetry transmitter that radiates a signal responsive to the optical detector. Fluorescence may thus be detected by the telemetry receiver at the base site without the use of high-power lasers or ultra-sensitive receivers. This method is particularly suitable for the detection of agents by means of UV fluorescence. The differential method described above can be used for discriminating against spurious background fluorescence. Moreover, a time delayed observation can be used for further discrimination. In this case, the receiver will be gated to respond at a delayed time with respect to the incident UV pulse. The delay is adjusted to take advantage of the fluorescence decay-time of the agent to be detected. This time delayed observation cannot be used to advantage in the previous systems for the remote sensing of fluorescence from an extended volume.

For biological agents, generally existing in the form of aerosol droplets, the natural UV fluorescence from protein molecules can provide the signatures needed for detection and identification. It is known that tryptophan residues in a protein molecule have two strong absorption peaks, one of which is centered at about 295 1 nm and the other at 235 nm. The fluorescence caused by an incident UV pulse within these absorption peaks occurs in the 350 nm range. The 350 nm fluorescence appears in two broad and overlapping emission bands with different decay times. These decay times are of the order of several nanoseconds. It is possible to generate UV laser pulses in the 200 nm to 300 nm region by harmonic generation of a tunable dye laser in the 400 nm to 600 nm range. The pumping laser to drive the dye laser may be a pulse laser of the kind described in my co-pending United States patent application Ser. No. 496,069 filed May 19, 1983, abandoned. With this method, UV pulses within the 295 or 235 tryptophan absorption peaks can be generated with a pulse duration of about two nanoseconds or less. A gated electronic detector with a gate-width of one to two nanoseconds at several nanoseconds delayed time can be used to observe the time-delayed 350 nm fluorescence. This makes it possible to obtain a time resolved spectrum of the tryptophan residue in the protein molecules. For detailed spectral signatures, a small grating with an array of detectors can be used to observe the fluorescence at a number of discrete wavelengths within the 350 nm fluorescence spectrum. The overlapping bands are also polarization sensitive. In the sensor, the behavior of observed time-delayed fluorescence versus wavelength, together with the polarization behavior of the fluorescence signals, can be used in diagnostics for discrimination against spurious background fluorescence. Moreover, in the presence of bacteria and viruses, the similarly obtained fluorescence signals will depend upon the specific bacterial or virus. These dependencies can be used in the diagnostics to specify the type of biological agent detected by the sensor.

In those instances where a chemical reaction is to be produced before examination for fluorescence, the sensor unit is provided with a supply of chemical reactant and arranged to spray the reactant into the area or onto the surface to be examined. The laser, chemical spray, and optical detection functions can be combined into a small unitary structure, the sensor unit, that can be projected or otherwise propelled into the area to be examined.

The sensor unit with spray chemical ability can also be used as a hand-held unit without need for the telemetry system where examination is to be made for a surface contaminate or a specific trace gas in the atmosphere.

In a preferred embodiment, the unit carries a reactant gas that is specific for a particular substance and produces a strongly fluorescing reaction product. The unit optically monitors for the fluorescence and provides a suitable visual or audible signal. The laser may be a pulsed unit of the kind described in my co-pending United States application Ser. No. 496,069, mentioned above, titled: "Laser System with Interchangeable Modules and Method for Changing such Modules". Such a unit may be battery-powered, generate the necessary laser light of such frequency and intensity as to be eye-safe in operation and, of major importance, low enough in cost to permit quantity usage.

BRIEF DESCRIPTION OF THE DRAWING

FIG. 1 is a diagrammatic representation of a remote sensing system in which telemetry signals are transmitted from a remote area being examined to a base site to provide information as to the presence of a specific chemical;

FIG. 2 shows the sensor of FIG. 1 being dropped by parachute to indicate the presence of an atmospheric contaminate at a remote location;

FIG. 3 shows certain details of another sensor unit suitable for projection into a remote area;

FIG. 4 illustrates an operation in which the sensor unit of FIG. 3 is projected or otherwise propelled into the area to be examined;

FIG. 5 is a diagrammatic illustration of a remote sensor unit adapted to produce a chemical reaction product, test the reaction product for fluoresence, and transmit the result;

FIG. 6 illustrates the battle field use of the sensor carried by a drone aircraft to detect nerve gas in a remote location; and FIG. 7 is a diagrammatic illustration of a portable battery-powered hand-held sensor arranged to carry a supply of chemical reactant, spray the reactant on a surface to be examined for contamination, radiate the area with laser light, and detect the presence or absence of fluorescence.

DESCRIPTION OF THE PREFERRED EMBODIMENTS

In the various figures, similar elements are indicated by the same numbers or by the same numbers followed by a differentiating suffix.

As illustrated by FIG. 1, a typical system for the detection of trace gases or suspended chemical substances includes a base site, generally indicated at 1, having a telemetry receiver 2 coupled to a receiving antenna 3, and an output indicator, shown diagrammatically at 6. At a position remote from the base site, in the vicinity of the area to be examined for the substance of interest, is a sensor unit, generally indicated at 12. The sensor unit 12 includes a low-power pulsed laser 14 that emits a laser beam having a wavelength suitable for producing fluorescence in the particular substance whose presence is to be determined or in a particular reaction product of that substance.

This laser 14 may be similar to the one mentioned above as described in my co-pending application. If the beam emitted by the laser illuminates the substance to be detected, the substance is caused to fluoresce and this fluorescence is detected by an optical-detection device 18 that forms part of the sensor unit 12. Optical detection devices capable of responding to fluorescence are well known along with means for adjusting the device for optimum response to the particular fluoresence that is expected and minimizing the effect of ambient illumination. When fluorescence is detected, a telemetry transmitter 22, operating in conjunction with a signal processor 46, that forms part of the sensor unit 12 is activated and caused to transmit, through an antenna 23, a telemetry signal to the receiving antenna 3 at the base site 1 where it produces a signal to activate the indicator 6.

In order to increase the sensitivity of the test, the substance to be detected may be concentrated prior to the examination. Nerve gas, for example, may be dispersed in tiny droplets with a density so low that direct detection is difficult. In this example, a duct 24 is provided with an exhaust fan 26 that forces a continuous flow of air from an intake screen 27 on the bottom of the unit through a filter 28 that collects the contaminate to be examined. A beam from the laser 14 illuminates the surface of the filter 28 which is examined for fluorescence by the optical detector 18. Information from the optical detector is transmitted to the base site by the transmitter 22.

In many instances, a more reliable and more sensitive result may be achieved by providing a chemical reactant capable of reacting with the substance to be detected to produce a reaction product that fluoresces strongly at the selected frequency of the laser light. For example, the filter 28 may comprise a pad of cotton or other porous material saturated with an indole sodium perborate solution or other reactant.

The specific components to be selected will depend upon the particular circumstances of use. For example, if the distance between the base site 1 and the remote location is not great, the telemetry antennas 3 and 23 may be non-directional and no particular orientation of the antennas will be necessary. For greater distances, known methods for achieving directivity in transmission and reception may be employed. In general, the sensor unit 12 will be located in a position where power is unavailable or, as described later, may actually be in flight while measurements are being made. For this reason, the operation of the sensor units is battery powered by a common battery power source 30 carried within the sensor unit package. The sensor unit assembly may be positioned at the remote site by any desired means: it may be hand-carried, dropped by parachute, carried by a drone plane or projected from a gun or other launching device.

Figure 2:
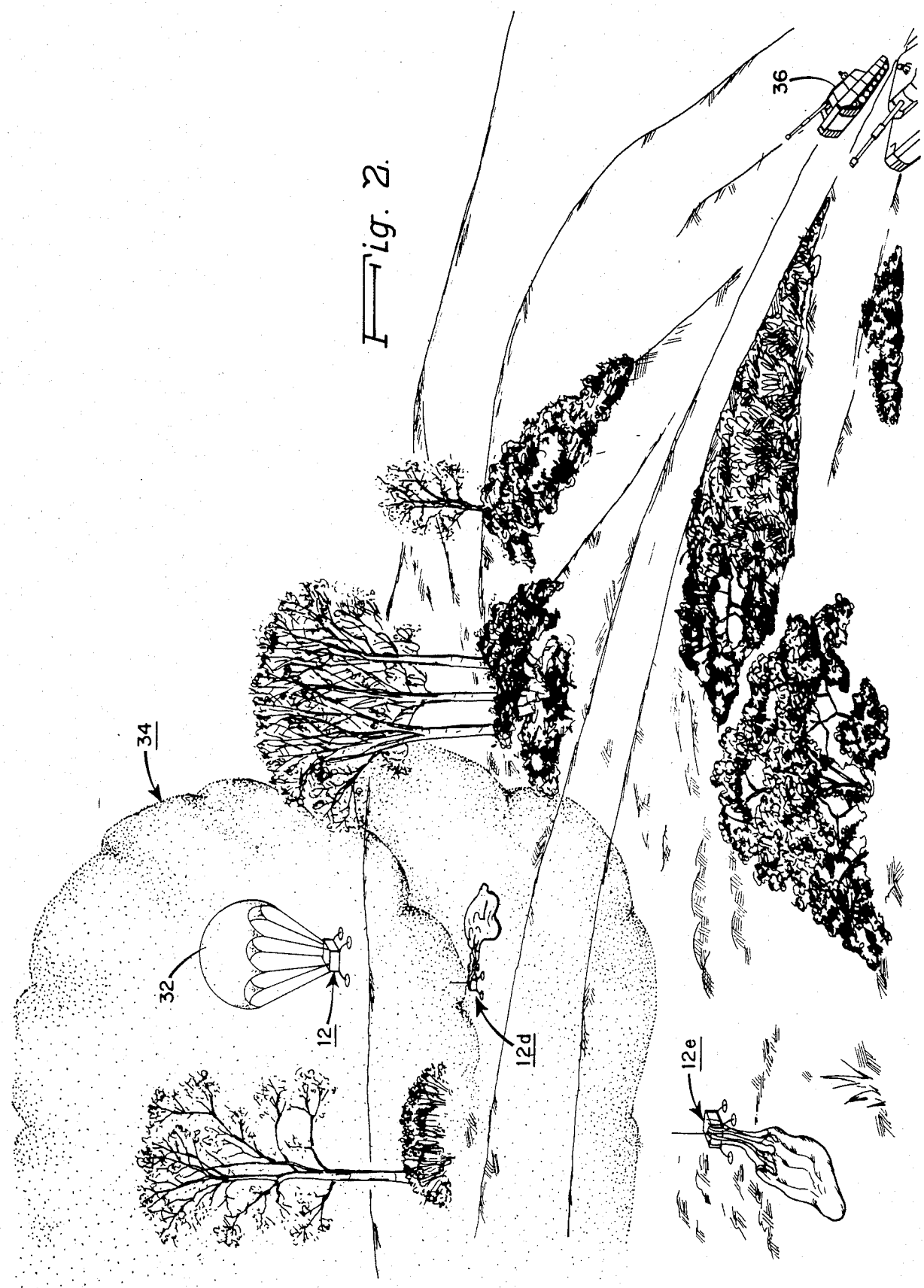

As shown in FIG. 2, in an actual field operation, the sensor unit 12 may be dropped by a parachute 32 into a cloud, generally indicated at 34, which is suspected of containing a specific contaminant. The unit 12 telemeters the presence or absence of the contaminate as it passes earthward through the cloud. This information is received at a base site, which in this instance may be a tank 36 or other military vehicle. After the unit lands on the earth, it may continue to examine the atmosphere and telemeter information to the base site. At the moment illustrated by FIG. 2, similar sensor units 12d and 12e are already on the ground and are continuing to examine the atmosphere for contaminates.

Figure 3:
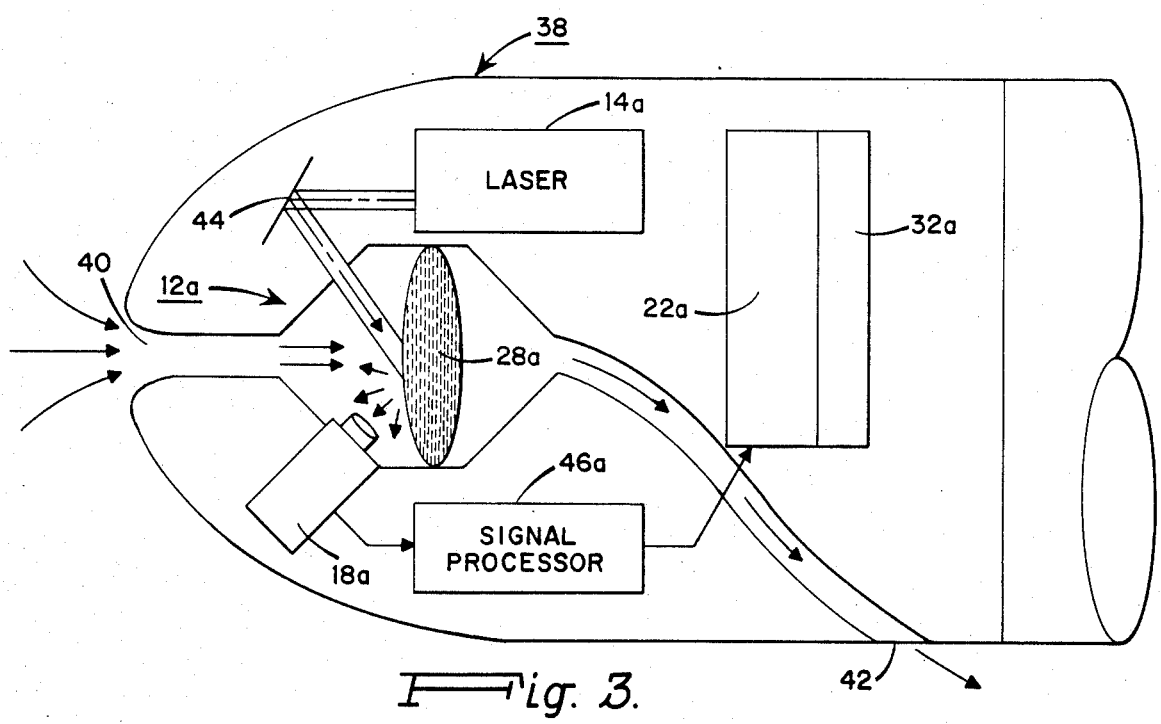

As shown in FIGS. 3 and 4, a sensor unit 12a, similar to the sensor unit 12, is arrranged to be incorporated into an artillery shell, generally indicated at 38. The sensor unit 12a has a nose opening 40 through which the atmosphere to be tested enters the sensor. While the shell 38 is in transit, the incoming air passes through a filter 28a and is exhausted through a port 42. The filter 28a, which may be saturated with a reactant chemical such as an indole sodium perborate solution, collects and concentrates the contaminate from the air stream. The filter 28a is illuminated by a laser beam from a source 14a that is reflected from a mirror 44. Fluorescence at the filter surface is detected by an optical detector 18a that together with a signal processor 46a produces a signal indicating the presence or absence of fluorescence at the filter 28a. This signal is transmitted to the base sight, in this instance a tank 36a, by a telemetry transmitter 22a. All components are powered by a battery pack 32a.

Figure 5:
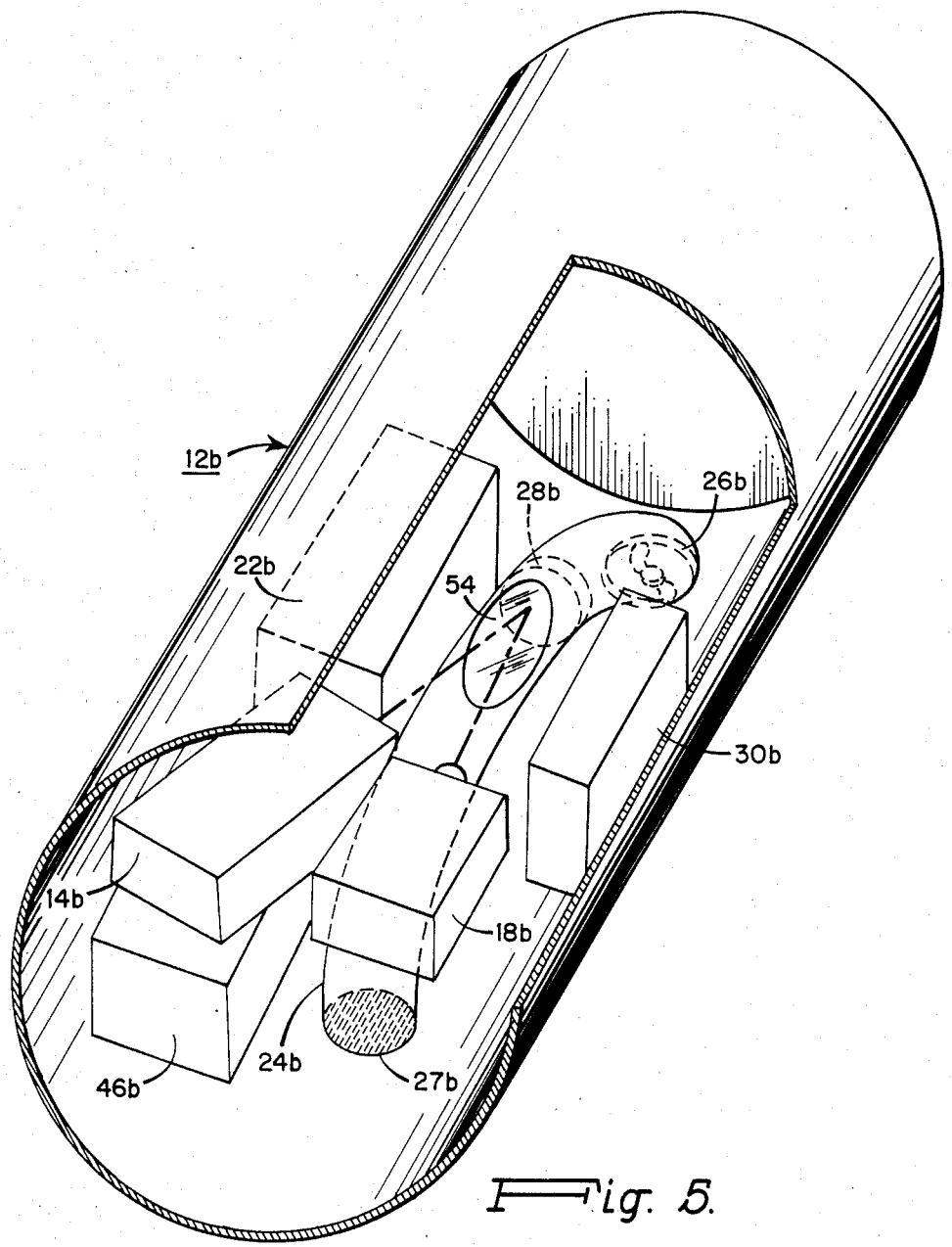
Figure 6:
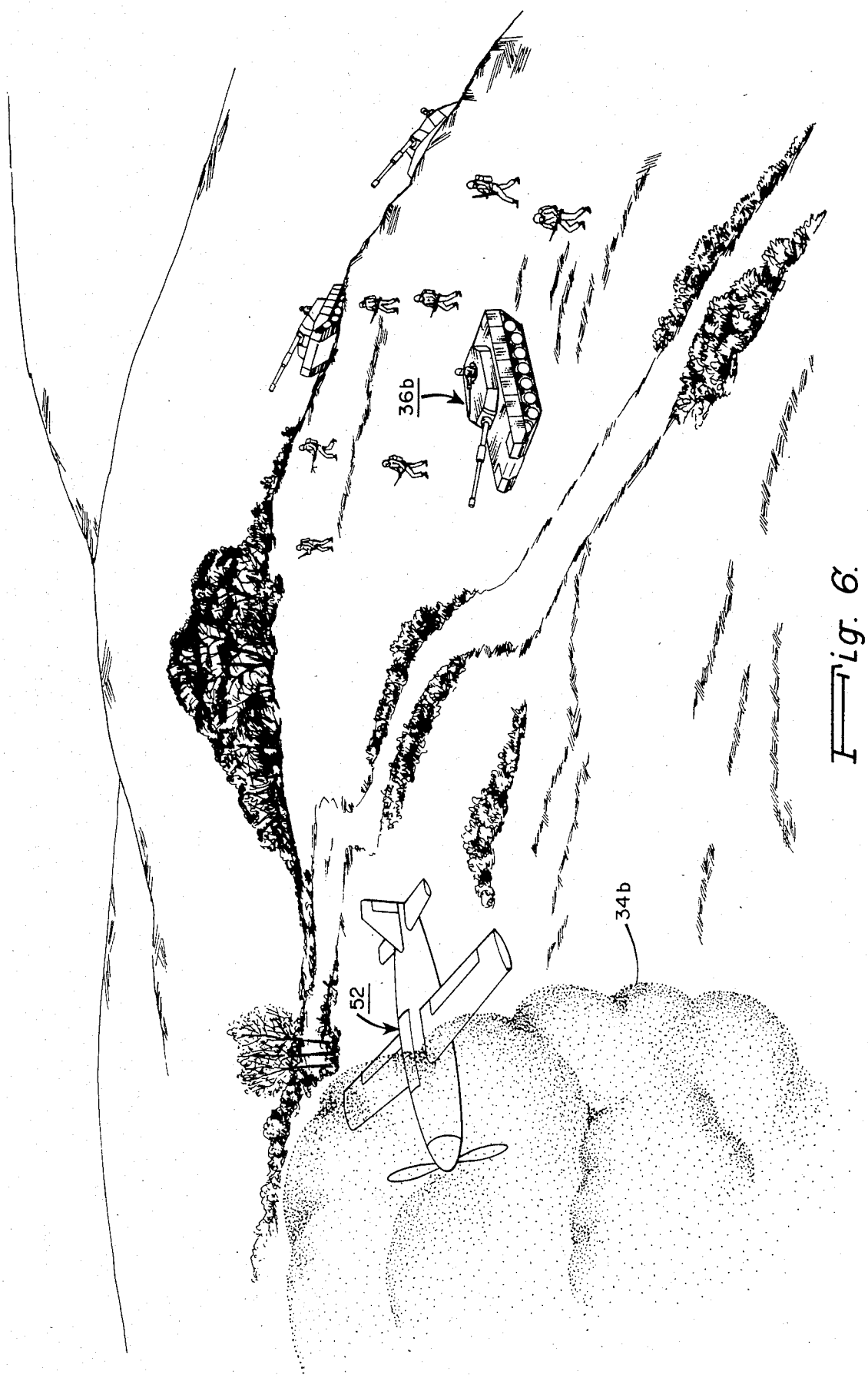

In operation, the tank 36a may fire a series of shells 38 in a forward direction to sample the air for contaminates as the tank moves forward. The telemetry system may include 2-way controls so that the sensor unit 12a is activated for operation by a signal transmitted from the tank 36a. The sensor 12a then collects a sample along a path length indicated at 48 and then examines the collected substance and transmits a telemetry signal to indicate the presence or absence of the suspected contaminate.

Where the distance between the base site and the area to be examined for the presence of a chemical substance is greater, or for other reasons, it may be desirable to provide continuing flight and orientation control for the sensor unit as illustrated by FIGS. 5 and 6. In this instance, a sensor unit 12b is carried by a drone aircraft 52 illustrated entering a cloud 34b to be examined for the presence of a particular contaminating substance. The base site 1, in this instance, may comprise a tank 36b or it may be a more remote location. The sensor may be carried by any remotely controlled projectile or other vehicle. The use of laser beams and other methods for controlling the path and orientation of such a projectile are well known and are not described in detail here.

The sensor unit 12b is mounted on the drone plane 52 in such manner that an intake screen 27b is exposed to the surrounding atmosphere which is drawn through a duct 24b by a fan 26b. A filter 28b, mounted in the duct 24b, collects the contaminating chemical which is then illuminated, through a window 54 in the duct 24b, by a laser 14b. As in the other examples, the filter may be saturated with a reactant chemical to increase the accuracy and sensitivity of the test. The filter surface is examined for fluorescence by an optical detector 18b which in conjunction with a signal processor 46b and a telemetry transmitter 22b transmits an appropriate signal to the base site at tank 36b.

In operation, the drone 52 is directed to the area to be examined. The laser 14b and the optical sensor 18b may operate continuously or may be turned on at the appropriate time by a signal from the base site 36b. The laser-detection assembly as used in the examples of FIGS. 1–6 becomes a disposable item returning data only while in flight through the area to be examined and, for that reason, the use of low cost components is a necessity. The system described here, making use of the low-cost laser previously referred to, meets that requirement.

FIG. 7 illustrates a hand-held sensor unit 12c which is generally similar to the sensor unit 12, but contains no transmitter or antenna. The release of the reactant spray through a nozzle 56 from a container 58 and activation of the laser 14c are initiated by a manually operated push-button 62. The spray is applied to a surface suspected of contamination, which is illuminated by the laser light. Any resulting fluorescence may in some instances be detected by visual examination and in other instances by the optical sensor 18c that may include a spike filter 64 and a photodetector 66 arranged to actuate a visual indicator, shown diagrammatically at 6c. The entire sensor unit is contained in a housing 68 provided with a handle 72 by which the sensor is supported while the surface suspected of contamination is being scanned. Although the hand-held unit of FIG. 7 does not require any communication channel with a base site, a telemetry channel may be included to permit auxiliary monitoring at the base site.

As used herein the term "remote location", and similar terms, mean a location removed from the reference point by a distance greater than the maximum distance over which fluorescence of the substance to be sensed can be produced by the particular laser being used and detected by the particular optical detection means being used, both at a common location.

It is apparent that various modifications of the system may be made to best fit the arrangement to each particular application without departing from the intended context of the invention. The foregoing examples are not intended to delineate the scope of the invention, which is to be limited only in accordance with the following claims.

What is claimed is:

1. Apparatus for remote sensing of a chemical substance responsive by fluorescence to laser light illumination comprising
   a sensor unit positioned adjacent an area to be examined for the substance including
   a laser arranged to illuminate at least a portion of said area to produce fluorescence from any of such substance present in the illuminated portion of said area,
   optical detection means responsive to said fluorescence,
   a storage chamber,
   a chemical reactant carried within said chamber and capable of reacting with a specific agent to produce said chemical substance,
   means for spraying said chemical reactant into said area, and
   a telemetry transmitter responsive to said optical detection means and arranged to radiate a signal having characteristics dependent upon the presence or absence of said fluorescence,
   a telemetry receiver positioned remotely from said sensor unit arranged to receive said signal, and
   indicator means coupled to said receiver and responsive to the signal received by said receiver.

2. Apparatus as claimed in claim 1 including
   a projectile incorporating said sensor unit, and
   launching means positioned remotely from the said area to be examined and capable of launching said projectile.

3. A portable sensor for sensing the presence of a contaminate on a surface by detecting the presence of a predetermined reaction product produced by a chemical reaction between said contaminate and a chemical reagent including
   a chamber having therein a supply of said chemical reagent,
   spray means for spraying said reagent on said surface thereby to produce said reaction product in the presence of said contaminate,
   a laser capable of illuminating said surface and causing fluorescence of said reaction product,
   optical detection means responsive to said fluorescence,
   indicator means under the control of said optical detection means for indicating the presence of said reaction product and thereby the presence of said contaminate,
   battery power supply means arranged to provide power for said laser, and said optical detection means, and
   a unitary housing containing said power supply means, said laser, said chamber and said optical detection means.

4. The method of detecting the presence of a chemical substance situated in a remote area comprising the steps of
   providing a telemetry receiver,
   positioning a sensor unit remotely from said receiver and in the vicinity of the area to be examined for the presence of said substance,
   discharging into said area from said sensor unit a chemical reaction agent capable of reacting with said substance to produce a reaction product capable of fluorescing,
   illuminating at least a portion of said area with laser light from said sensor unit capable of causing said reaction product to fluoresce,
   optically detecting at said sensor unit the presence or absence of fluoresence by said reaction product,
   radiating from said detection assembly a telemetry signal responsive to said optical detection, and
   receiving said signal at said telemetry receiver.

5. The method as claimed in claim 4 including the steps of
   providing launching means positioned remotely from said remote area where said chemical substance is to be detected, and
   launching said sensor unit into said remote area.

* * * * *